United States Patent [19]

Sumi et al.

[11] Patent Number: 5,369,020
[45] Date of Patent: Nov. 29, 1994

[54] METHOD FOR SUPPRESSING COLORING OF HUMAN SERUM ALBUMIN

[75] Inventors: Akinori Sumi; Wataru Ohtani; Naoto Furuhata; Kazuya Takeshima; Kaeko Kamide; Takao Ohmura; Kazumasa Yokoyama, all of Hirakata, Japan

[73] Assignee: The Green Cross Corporation, Osaka, Japan

[21] Appl. No.: 31,823

[22] Filed: Mar. 16, 1993

[30] Foreign Application Priority Data

Mar. 16, 1992 [JP] Japan .................................. 4-091624

[51] Int. Cl.$^5$ .......................... C12P 1/02; C12P 21/02
[52] U.S. Cl. ................................... 435/69.6; 435/171; 530/364
[58] Field of Search ..................... 435/69.1; 530/412; 210/917

[56] References Cited

U.S. PATENT DOCUMENTS

| | | | |
|---|---|---|---|
| 4,054,489 | 10/1977 | Zhdanova et al. | 435/111 |
| 4,086,222 | 4/1978 | Lindquist et al. | 530/364 |
| 4,165,258 | 8/1979 | Pye et al. | 435/215 |
| 5,135,736 | 8/1992 | Anderson et al. | 424/1.49 |

FOREIGN PATENT DOCUMENTS 0464590 1/1992 European Pat. Off. .
0570916 11/1993 European Pat. Off. .

OTHER PUBLICATIONS

Quirk, A. V. et al.; Biol. Abstracts 88:36945 (1989).
Sreekrishna et al.; Biochemistry 28:4117–4125 (1989).
Kemp, D. S. et al.; Organic Chemistry, Worth Publishers Inc., NY (1980) pp. 412–414.

*Primary Examiner*—Robert A. Wax
*Assistant Examiner*—Eric Grimes
*Attorney, Agent, or Firm*—Sughrue, Mion, Zinn, Macpeak & Seas

[57] ABSTRACT

A method for suppressing coloring of human serum albumin expressed by genetic engineering, which comprises culture and/or purification in the presence of an amine compound selected from the group consisting of alkylamines, diamines, guanidines, benzamidines, basic amino acids, and aminophenylacetic acids. According to the present invention, coloring of HSA expressed by genetic engineering can be suppressed to from one-half to one-tenth of that without treatment for coloring suppression. In addition, HSA can be recovered in high yields, and the treatment of the invention does not affect the inherent properties of HSA.

7 Claims, No Drawings

METHOD FOR SUPPRESSING COLORING OF HUMAN SERUM ALBUMIN

FIELD OF THE INVENTION

The present invention relates to a method for suppressing coloring of human serum albumin expressed by genetic engineering.

BACKGROUND OF THE INVENTION

An albumin, particularly human serum albumin (hereinafter also referred to as HSA) is an important component constituting protein in plasma. This protein is produced in liver, and is mainly responsible for sustaining normal osmotic pressure of blood flow. Also, it functions as a carrier for various serum molecules.

HSA is administered in a variety of clinical situations. For example, when HSA is administered to a patient suffering from shock or ambustion, it functions to recover blood volume to its original level, thereby improving some symptoms relating to trauma. For this effect, HSA is frequently administered. Also, patients suffering from hypoproteinemia or fetal erythroblastosis may need treatments with HSA. As exemplified, the basic significance of HSA administration is prominent in the treatment of symptoms accompanying loss of fluids from blood vessels, as in surgery, shock, burn, or hypoproteinemia which causes edema.

At present, HSA is produced mainly by fractionation of blood. This production method is uneconomical, and besides, it poses a problem that the supply of the blood from which HSA is produced is not always assured. Moreover, since HSA is blood-originated, HSA produced in this way is under a constant risk of containing undesirable substances such as hepatitis viruses. From this aspect also, development of a substitute for blood as the raw material for HSA will be greatly advantageous.

Under the circumstances as described, methods for a large-scale production of HSA by genetic engineering, followed by high purification is being established. Such method will permit economical production of HSA containing no undesirable substances such as hepatitis viruses.

By genetic engineering, however, HSA is colored by being combined with a certain coloring component present in raw materials or by the contamination of substances secreted by microorganisms during culture of host microorganisms and/or during purification of HSA. These contaminants cannot be removed sufficiently by conventional purification methods for plasma-originated HSA.

SUMMARY OF THE INVENTION

Accordingly, the object of the present invention is to provide a method for suppressing coloring of HSA which is caused by medium components or cell secrete, when producing HSA by genetic engineering.

The present inventors conducted various studies for achieving the object as described, and have found that by carrying out, in the presence of a particular amine compound, culture and/or purification for the production of HSA by genetic engineering, coloring of HSA which is caused by the combination of or reaction between HSA produced extracellularly by genetic engineering and coloring materials can be suppressed, and completed the invention.

Accordingly, the present invention relates to a method for suppressing coloring of human serum albumin expressed by genetic engineering, which comprises conducting culture and/or purification in the presence of a specific amine compound from the group of alkylamines, diamines, guanidines, benzamidines, basic amino acids, and aminophenylacetic acids.

DETAILED DESCRIPTION OF THE INVENTION

The present invention relates to a method for suppressing coloring of HSA to be produced by genetic engineering, which comprises culturing cells (e.g. *Escherichia coli*, yeast, *Bacillus subtilis*, koji, animal cells) capable of expressing HSA, followed by extracellular expression (secretory expression).

1. Preparation of HSA-producing host by genetic engineering

The HSA-producing host to be used in the present invention is subject to no particular limitation so long as it is prepared by genetic engineering, and any host whether disclosed in known literatures or to be developed in the future may be appropriate provided that it is capable of achieving the object of the invention. Specific examples of suitable hosts imparted with HSA producibility by genetic engineering are *Escherichia coli*, yeast, *Bacillus subtilis*, and animal cells. Particularly in the present invention, the use of a yeast, specifically the genus Saccharomyces (e.g. *Saccharomyces cerevisiae*) or the genus Pichia (e.g. *Pichia pastoris*) as a host is desirable. Also, auxotroph strains or antibiotic sensitive strains can be used. In addition, the *Saccharomyces cerevisiae* AH22 strain (a, his 4, leu 2, can 1) or *Pichia pastoris* GTS115 strain (his 4) can be preferably used.

The method for the preparation of these HSA-producing hosts, the method for producing HSA by culturing the hosts, and the method for the separation and harvesting of HSA from cultures may be known or those analogous thereto. For example, methods for the preparation of HSA-producing host (or HSA-producing strain) include a method wherein a known human serum albumin gene is used (European Patent Publication Nos. 73646, 79739 and 206733), a method wherein a new human serum albumin gene is used (Japanese Patent Unexamined Publication Nos. 29985/1987, 98486/1989), a method wherein a synthetic signal sequence is used (European Patent Publication No. 329127), a method wherein serum albumin signal sequence is used (European Patent Publication No. 319641), a method wherein a recombinant plasmid is incorporated on chromosome (European Patent Publication No. 399455), a method wherein hosts are fused (European Patent Publication No. 409156), a method wherein mutation is caused in a medium containing methanol, a method wherein variant $AOX_2$ promoter obtained by modifying natural $AOX_2$ promoter by, for example, partial deletion, substitution or addition of its base sequence to improve activity as a promoter, is used (Japanese Patent Application Nos. 63598/1991, 63559/1991), an expression of HSA by *Bacillus subtilis* (Japanese Patent Unexamined Publication No. 25133/1987), a production of HSA with yeast (European Patent Publication Nos. 123544, 248637 and 251744), a production of HSA with Pichia (European Patent Publication No. 344459), and the like.

Of the methods mentioned above, the method wherein mutation is caused in a medium containing methanol comprises the following steps. That is, a plasmid having a transcription unit where HSA is expressed under the control of $AOX_1$ promoter is introduced into a suitable host, preferably a Pichia yeast, specifically into an $AOX_1$ gene region of GTS115 strain (NRRL deposit No. Y-15851) by a conventional method to obtain a transformant (see European Patent Publication No. 344459). This transformant shows poor growth in a medium containing methanol. Then, this transformant is cultured in a medium containing methanol to cause mutation, and only strains which show rapid growth are collected. The methanol concentration is about 0.0001–5%, and the medium may be artificial or natural. Incubation is conducted at 15°–40° C. for 1–1000 hours.

The methods for the culture of an HSA-producing host, namely, production method for HSA, include a method wherein high concentration cells and yield products are obtained by supplying a suitably small amount of high concentration glucose, etc. by a fed-batch culture so as to avoid an inhibition effect caused by high concentration substrate, on the yielded cells (Japanese Patent Application No. 219561/1989), a method wherein HSA production is enhanced by adding fatty acid in medium (Japanese Patent Application No. 81719/1991), and other methods besides the methods described in the above publications.

The methods for the separation and harvesting of HSA include, for example, inactivation of protease by heat treatment (European Patent Publication No. 420007) and suppression of coloring by separating HSA from coloring components with the use of at least one member of the group of anion exchanger, hydrophobie carrier, and active charcoal (Japanese Patent Unexamined Publication No. 54198/1992).

The medium to be used for the cultivation of a transformant host is a medium known in this field which has been supplemented with a fatty acid having 10–26 carbon atoms or its salt, and cultivation can be conducted by a conventional method. The medium may be synthetic or natural, with preference given to a liquid medium. For example, synthetic medium may contain various sugars as carbon sources; urea, ammonium salt nitrate, etc. as nitrogen sources; various vitamins and nucleotide as micronutrients; and Mg, Ca, Fe, Na, K, Mn, Co, Cu, etc. as inorganic salts, and is exemplified by YNB liquid medium [0.7% yeast nitrogen base (manufactured by Difco), 2% glucose]. Examples of natural medium include YPD liquid medium [1% yeast extract (manufactured by Difco), 2% Bacto-peptone (manufactured by Difco), 2% glucose]. The pH of the medium may be neutral, weak basic, or weak acidic. When a host utilizes methanol, a medium containing methanol can be used. In this case, the methanol concentration is about 0.01–5%.

The incubation temperature is preferably 15°–43° C. (20°–30° C. for yeasts, and 20°–37° C. for bacteria). The incubation is conducted for about 1 to 1000 hours, under aeration, by batch culture, fed-batch culture, or continuous culture, with allowing to stand, shaking, or stirring. Preculture in advance of main culture is preferable, wherein used is, for example, YNB liquid medium or YPD liquid medium. The preculture is conducted for 10 to 100 hours at 30° C. for yeasts and 37° C. for bacteria.

After culture, HSA is harvested from culture filtrate or cells by known separation and purification methods.

2. Step for suppressing combination or reaction of HSA with coloring materials

The step for suppressing coloring of HSA is incorporated into culture step, (post-culture) purification step, and/or line steps (steps from culture to purification completely automated without hand operation), and applied to an HSA-containing aqueous solution such as culture solution, culture supernatant, crude purification fraction, purified fraction, or the like.

In the present invention, combination or reaction of HSA expressed by culture, with coloring materials can be suppressed by conducting the above-mentioned treatment(s) in the presence of a specific compound to be mentioned below. This suppressing step is desirably conducted during the culture step in case of extracellular expression. The compound to be used for the color suppression is amine compound.

As the amine compound, exemplified are alkylamines, diamines, guanidines, benzamidines, basic amino acids, and aminophenylacetic acids. The alkylamines preferably have 1-6 carbon atoms, and include, for example, methylamine, ethylamine propylamine, isopropylamine, and butylamine. Examples of the diamines include alkylenediamines (particularly those having 1 to 6 carbon atoms, such as methylenediamine, ethylenediamine, and propylenediamine), and N,N-dialkylalkylenediamines (particularly alkyls and alkylenes having 1-6 carbon atoms, such as N,N-dimethylethylenediamine and N,N-diethylethylenediamine). Examples of the guanidines include guanidine, aminoguanidine, and phenylguanidine. The benzamidines are exemplified by benzamidine, p-aminobenzamidine, etc. The basic amino acids are exemplified by lysine and arginine.

The suppression of coloring in the culture step is suitably conducted under the following conditions.

pH: 4–9 (preferably pH 5–7) proportion of amine compound to be added: 0.01–10 w/v%, preferably 0.1–1 w/v% relative to medium Also, the suppression of coloring in the present invention may be conducted during the purification of HSA. The purification may be carried out by known methods such as various fractionations, adsorption chromatography, affinity chromatography, gel filtration, density gradation centrifugation, and dialysis.

The suppression of coloring during the purification step can be carried out under the following conditions.

pH: 4–9 (preferably pH 5–7) proportion of amine compound to be added: 0.01–10 w/v%, preferably 0.1–1 w/v% relative to HSA-containing liquid fraction The present invention is hereinafter described in detail by referring to examples, by which the present invention is not limited.

EXAMPLES 1–7

1. Strain used: *Saccharomyces cerevisiae* TMS33-1h4 strain

The histidine prototrophy revertant TMS-33-1h4 strain was obtained in the following manner from the histidine auxotrophy TMS-33-1 strain prepared according to Japanese Patent Unexamined Publication No. 72889/1991. After TMS-33-1 strain was grown overnight in a non-selective medium, cells were collected, washed thoroughly, and coated on a selective plate (a plate of a medium without histidine). The selective plate was cultured at 30° C., and TMS-33-1h4 strain was obtained from the revertant candidate strains grew.

2. Medium i) YNB medium: Bacto-Yeast Nitrogen Base (6.7 g, manufactured by Difco) dissolved in 100 ml of distilled water and sterilized by filtration, was mixed with 20 g of glucose (manufactured by Nakarai Kagaku, Japan) dissolved in distilled water to make the total amount 900 ml and then autoclaved.

ii) Glucose-ammonium acetate synthetic medium: having the composition of Table 1

TABLE 1

| Component | Concentration (mg/L) |
|---|---|
| Glucose | 20,000 |
| $CH_3COONH_4$ | 5,000 |
| $KH_2PO_4$ | 10,000 |
| $CaCl_2\ 2H_2O$ | 100 |
| KCl | 2,000 |
| NaCl | 100 |
| $MgSO_4\ 7H_2O$ | 2,000 |
| $ZnSO_4\ 7H_2O$ | 100 |
| $CuSO_4\ 5H_2O$ | 5 |
| $FeCl_3\ 6H_2O$ | 100 |
| Biotin | 0.1 |
| Vitamin $B_1$ | 10 |
| Vitamin $B_6$ | 1 |
| Sodium pantothenate | 10 |
| Inositol | 50 |
| | pH 6.0 | iii) Culture
Preculture

A suitable amount of TMS-33-1h4 strain was inoculated into a YNB medium-containing Erlenmeyer flask equipped with baffles, and subjected to shaking culture at 30° C. for 24 hours.

Main culture

The preculture was centrifuged, and cells were collected. The cells were suspended in 10 ml of sterilized water. The cell suspension (1 ml) was inoculated into glucose-ammonium acetate synthetic medium (100 ml). The culture medium (100 ml) was dispensed to a 300 ml Erlenmeyer flask equipped with baffles, and subjected to shaking culture at 30° C. for 70 hours at 125 rpm.

On that occasion, various amine compounds as indicated in Table 2 were respectively added in culture. For comparison, culture was carried out without amine compounds (reference).

iv) Experiment Example (Effect of various amine compounds added in culture media, on coloring of HSA)

Purification of Culture Supernatant and Concentration

After culture, a sample was taken from each culture medium. The sample was centrifuged at 15,000 rpm for 5 minutes, and a part of the supernatant obtained was determined for HSA concentration.

To the remaining culture supernatant (about 100 ml) was added Blue Cellulofine (1 g, washed thoroughly with physiological saline, manufactured by Seikagaku Kogyo, Japan) as a filter cake, and albumin was allowed to adsorb thereon at room temperature for 2 hours. The Blue Cellulofine on which albumin had been adsorbed was transferred to a minicolumn, washed with physiological saline, and eluted with 3 ml of 3M sodium thiocyanate. The eluate was concentrated in a concentrator [Centricon 30 (30K), manufactured by Amicon], and used as a sample for measurement.

Measurement of HSA

HSA concentration in culture supernatant was determined by reversed passive hemagglutination assay (RPHA), based on which the HSA amount was determined. The amount of HSA was expressed as a ratio on a standard HSA (manufactured by Miles) basis, taking the HSA amount therein as 1.

Degree of Coloring

The purified and concentrated samples were examined for the absorbance at a wavelength of 280 nm, 350 nm, or 405 nm. The ratio of the absorbance at the wavelength of 350 nm to that at the wavelength of 280 nm, and that at the wavelength of 405 nm to that at the wavelength of 280 nm were calculated, and used as indices for the degree of coloring. The results are summarized in Table 2.

TABLE 2

| | Coloring inhibitor (concentration w/v %) | 350 nm/ 280 nm | 405 nm/ 280 nm | HSA amount* |
|---|---|---|---|---|
| Reference | | 0.125 (100) | 0.113 (100) | 1 |
| Ex. 1 | Ethylenediamine (0.5) | 0.025 (20.0) | 0.013 (11.5) | 1 |
| Ex. 2 | Ethylenediamine (1.0) | 0.010 (8.0) | 0.007 (6.2) | 0.7 |
| Ex. 3 | Aminoguanidine (0.5) | 0.035 (28.0) | 0.015 (13.3) | 1 |
| Ex. 4 | Aminoguanidine (1.0) | 0.028 (22.4) | 0.010 (8.8) | 1 |
| Ex. 5 | N,N-diethylethylene-diamine (1.0) | 0.011 (8.8) | 0.009 (8.0) | 1 |
| Ex. 6 | N,N-dimethylethylene-diamine (1.0) | 0.011 (8.8) | 0.008 (7.1) | 1 |
| Ex. 7 | Aminophenylacetic acid (0.5) | 0.062 (49.6) | 0.057 (50.4) | 0.5 |

Note:
*expressed as a ratio taking the amount of HSA in Reference as 1

EXAMPLE 8

1. Strain used: The same strains used in Examples 1–7

2. Medium i) medium for batch culture: having the composition of Table 3 ii) medium for feed culture: having the composition of Table 4

TABLE 3

| Component | Concentration (mg/L) |
|---|---|
| Glucose | 1,000 |
| $(NH_4)_2SO_4$ | 2,000 |
| $KH_2PO_4$ | 20,000 |
| KCl | 4,000 |
| NaCl | 400 |
| $MgSO_4\ 7H_2O$ | 4,000 |
| $CaCl_2\ 2H_2O$ | 100 |
| $ZnSO_4\ 7H_2O$ | 100 |
| $CuSO_4\ 5H_2O$ | 10 |
| $FeCl_3\ 6H_2O$ | 100 |
| Biotin | 0.2 |
| Vitamin $B_1$ | 20 |
| Vitamin $B_6$ | 2 |
| Sodium pantothenate | 20 |
| Inositol | 100 |
| | pH 5.8 |

TABLE 4

| Component | Concentration (mg/L) |
|---|---|
| Glucose | 500,000 |
| $MgSO_4\ 7H_2O$ | 20,000 |
| $ZnSO_4\ 7H_2O$ | 1,000 |
| $CaCl_2\ 2H_2O$ | 300 |

TABLE 4-continued

| Component | Concentration (mg/L) |
|---|---|
| $CuSO_4 \cdot 5H_2O$ | 50 |
| Biotin | 1 |
| Vitamin $B_1$ | 100 |
| Vitamin $B_6$ | 10 |
| Sodium pantothenate | 100 |
| Inositol | 500 |

3. Culture

Preculture

Glycerol frozen stock cell line (1 ml, $OD_{540}=10$) was inoculated into a YNB medium-containing Erlenmeyer flask equipped with baffles, and subjected to shaking culture at 30° C. for 24 hours. After centrifugal harvesting, cells were suspended in sterilized water, and inoculated into a 4 L batch culture medium.

Main Culture

A 10 L mini-jar fermenter was used, and the culture was conducted with aeration and agitation. Aeration rate was set for 1 vvm, and agitation speed was controlled such that a dissolved oxygen concentration is not less than 10 ppm. The pH thereof was kept at 5.8 by adding 28% aqueous ammonia. Antifoaming was performed by adding a small amount of a antifoaming agent (Adekanol, manufactured by Asahi Denka Kogyo, Japan) as necessary. A feed medium (4 L) was added in accordance with a control program such that a specific growth rate becomes 0.12 ($hr^{-1}$).

Culture Control Program

The feed rate was controlled according to a program. The program usually sets the feed rate such that the specific growth rate becomes 0.12 ($hr^{-1}$). However, when the dissolved oxygen concentration falls to 2 or below while the culture is under control, the specific growth rate is set for 0 to maintain constant feed rate.

Amine Compound

Aminoguanidine (guaranteed, manufactured by Wako Junyaku, Japan) was added to the batch medium and the feed medium respectively such that the concentration thereof was 0.6 w/v%.

As a reference, culture was conducted without aminoguanidine.

4. Experiment Example—HSA production in the presence of amine compound, and its effect on coloring i) Determination of cell concentration A sample was taken from a culture medium at an optional time, and the sample was appropriately diluted with distilled water. The absorbance at 540 nm was measured by a spectrophotometer (UV 240, manufactured by Shimazu, Japan), and dry cell weight was determined from the calibration curve drawn in advance.

In the same manner as described, HSA concentration and degree of coloring were compared. The HSA concentration in the sample was expressed by mg/L. The results are tabulated in Table 5.

TABLE 5

|  | Reference | Example 8 |
|---|---|---|
| Culture time (hr) | 72 | 75 |
| $OD_{540}$ | 960.0 | 972.0 |
| Cell concentration (g-DCW/L) | 120.0 | 121.5 |
| HSA concentration (mg/L) | 800 | 800 |
| Degree of coloring | 0.165 (100) | 0.036 (21.8) |
| 350 nm/280 nm 405 nm/280 nm | 0.132 (100) | 0.022 (16.7) |

Culture proceeded smoothly in the presence of 0.6 w/v% aminoguanidine. The cell amount reached 120 g-DCW/L, and HSA production reached 800 mg/L by 72–75 hours of culture.

In other words, conventional culture (culture without the treatment for coloring suppression) could be carried out even in the presence of 0.6 w/v% aminoguanidine, and coloring of the HSA obtained showed about one-fifth of the coloring usually; observed (in the culture without the treatment for coloring suppression).

EXAMPLES 9–11

1. Strain to be used: *Pichia pastoris* GCP101

PC4130 can be obtained by replacing the $AOX_1$ gene region of *Pichia pastoris* GTS115 (his 4) (NRRL Y-15851) with the fragments cleaved with Not 1 of plasmid pPGP1 having a transcription unit where HSA expresses under the control of $AOX_1$ promoter, by the method as described in European Patent Publication No. 344359. Due to the absence of the $AOX_1$ gene, this strain shows poor growth in a medium containing methanol as a carbon source (Mut− strain).

PC4130 was inoculated into 3 ml of YPD medium (1% yeast extract, 2% Bacto-peptone, 2% glucose), and 24 hours later, it was inoculated into 50 ml of YPD medium at a concentration that made the initial $OD_{540}$ 0.1. After incubation at 30° C. for 3 days, it was inoculated into 50 ml of YPD medium at a concentration that made the initial $OD_{540}$ 0.1. The same subculture was repeated every three days. At every subculture, cells were diluted with sterilized water to make the cell concentration $10^7$ cells/plate, and coated on a 2% MeOH-YNB w/o a. a. plate (0.7% yeast nitrogen base without amino acid, 2% methanol, 1.5% agar powder). After incubation at 30° C. for 5 days, presence or absence of colony was observed. Twenty colonies were formed on a 2% MeOH-YNB w/o a. a. plate which had been coated with cells after 12 days' subculture. Mut− strain hardly formed colony on this plate, but Mut+ strain could form one. That is, the colony formation on this plate indicates enhanced utilization of methanol, and it also indicates that a strain converted to Mut+ could be obtained. One of the colonies formed was appropriately diluted with sterilized water, and spread on a 2% MeOH-YNB w/o a. a. plate into a single colony which was named GCP101.

2. Medium i) medium for preculture

Bacto-Yeast Nitrogen Base (6.7 g, manufactured by Difco) was dissolved in water to make the entire amount 100 ml, and 10×YNB which was sterilized and filtered, 20% glucose which was sterilized in an autoclave, and sterilized water were mixed at the ratio of 1:1:8 (v) and used.

ii) medium for main culture

Various amine compounds were respectively added to a medium containing methanol and glycerol as carbon sources (Table 6), and used as a medium for the main culture (pH 6.0).

TABLE 6

| Component | Concentration (1/l) |
|---|---|
| methanol | 40 ml |
| glycerol | 1,000 mg |
| ammonium acetate | 5,000 mg |
| $KH_2PO_4$ | 10,000 mg |
| $CaCl_2 \cdot 2H_2O$ | 100 mg |
| KCl | 2,000 mg |
| NaCl | 100 mg |
| $MgSO_4 \cdot 7H_2O$ | 2,000 mg |
| $ZnSO_4 \cdot 7H_2O$ | 100 mg |
| $CuSO_4 \cdot 5H_2O$ | 5 mg |
| $FeCl_3 \cdot 6H_2O$ | 100 mg |
| biotin | 0.1 mg |
| vitamin $B_1$ | 10 mg |
| vitamin $B_6$ | 1 mg |
| pantothenic acid sodium | 10 mg |
| inositol | 50 mg |

3. Method of culture i) preculture

One ml from stored 20% glycerol frozen vial was inoculated into 100 ml of YNB broth, and the broth was subjected to shaking culture in a 300 ml Erlenmeyer flask equipped with baffles at 30° C. for 24 hours.

ii) main culture

After 100 ml of the preculture was subjected to centrifugal harvesting, it was suspended in 10 ml of sterilized water. The cell suspension (0.5 ml) was inoculated into 50 ml of main culture. The culture medium (50 ml) was each dispensed to a 300 ml Erlenmeyer flask equipped with baffles, and subjected to shaking culture at 30° C. for 120 hours at 125 rpm.

The effect of various amine compounds on the coloring of HSA was examined by a method similar to that in Examples 1–7. The results are summarized in Table 7.

TABLE 7

| | Coloring inhibitor (concentration w/v %) | 350 nm/ 280 nm | 405 nm/ 280 nm | HSA amount* |
|---|---|---|---|---|
| Reference | | 0.098 (100) | 0.088 (100) | 1 |
| Ex. 9 | Ethylenediamine (0.6) | 0.011 (11.2) | 0.006 (6.8) | 0.8 |
| Ex. 10 | Aminoguanidine (0.6) | 0.016 (16.3) | 0.010 (11.4) | 1 |
| Ex. 11 | N,N-diethylethylenediamine (0.6) | 0.014 (14.3) | 0.009 (10.2) | 1 |

Note:
*expressed as a ratio taking the HSA amount in Reference as 1

According to the present invention, coloring of HSA expressed by genetic engineering can be suppressed to from one-second to one-tenth of that without the treatment for coloring suppression. In addition, HSA can be recovered in high yields, and the treatment of the invention does not affect the inherent properties of HSA.

Since the method of the present invention comprises addition of an agent for suppressing coloring of HSA during culture and/or purification, the method can be easily and efficiently performed.

Accordingly, the HSA treated by the method of the present invention can be used as a clinically useful pharmaceutical, as is plasma-originated HSA.

What is claimed is:

1. In a method for producing human serum albumin expressed by genetic engineering, the improvement which comprises culturing recombinant host cells expressing human serum albumin and/or purifying the expressed human serum albumin in the presence of an amine compound selected from the group consisting of diamines, selected from the group consisting of alkylenediamines having 1 to 6 carbon atoms and N,N-dialkylenediamines having 1 to 6 carbon atoms, guanidines, and aminophenylacetic acids.

2. The method for producing human serum albumin according to claim 1, wherein the diamines consist of methylenediamine, ethylenediamine, propylenediamine, N,N-dimethylethylenediamine, and N,N-diethylethylenediamine.

3. The method for producing human serum albumin according to claim 1, wherein the guanidines consist of guanidine, aminoguanidine, and phenylguanidine.

4. The method for producing human serum albumin according to claim 1, wherein the amine compound is added in a proportion of 0.1–10 w/v%.

5. The method for producing human serum albumin according to claim 1, comprising culturing, in a medium supplemented with the amine compound, recombinant human serum albumin-producing host cells prepared by genetic engineering.

6. The method for producing human serum albumin according to claim 5, wherein the recombinant human serum albumin-producing host cells are yeast cells.

7. The method for producing human serum albumin according to claim 6, wherein the yeast host cells belong to the genus Saccharomyces or the genus Pichia.

* * * * *